United States Patent
Greim

(10) Patent No.: US 8,207,737 B2
(45) Date of Patent: Jun. 26, 2012

(54) STANDING WAVE BARRIER FOR A MAGNETIC RESONANCE TOMOGRAPHY DEVICE

(75) Inventor: Helmut Greim, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 236 days.

(21) Appl. No.: 12/640,263

(22) Filed: Dec. 17, 2009

(65) Prior Publication Data

US 2010/0148775 A1    Jun. 17, 2010

(30) Foreign Application Priority Data

Dec. 17, 2008    (DE) .......................... 10 2008 063 458

(51) Int. Cl.
*G01V 3/00* (2006.01)
*H01P 7/04* (2006.01)
(52) U.S. Cl. ......... 324/322; 324/318; 324/309; 333/222
(58) Field of Classification Search .......... 324/300–322; 333/33, 219–235; 382/128–131; 600/407–435; 331/45, 57, 107 SL; 455/523; 606/33
See application file for complete search history.

(56) References Cited

U.S. PATENT DOCUMENTS

| | | | |
|---|---|---|---|
| 2,891,221 A * | 6/1959 | Bird et al. ........................ | 324/95 |
| 3,439,294 A * | 4/1969 | Flanagan et al. ................ | 333/33 |
| 3,795,855 A * | 3/1974 | Browning ...................... | 324/322 |
| 3,829,767 A * | 8/1974 | Delogne ......................... | 455/523 |
| 4,783,629 A * | 11/1988 | Arakawa et al. ............... | 324/322 |
| 5,461,314 A * | 10/1995 | Arakawa et al. ............... | 324/318 |
| 5,483,158 A * | 1/1996 | van Heteren et al. ......... | 324/318 |
| 5,565,779 A * | 10/1996 | Arakawa et al. ............... | 324/318 |
| 6,822,846 B2 | 11/2004 | Reykowski ..................... | 361/303 |
| 7,236,060 B2 * | 6/2007 | Wood .............................. | 331/57 |
| 8,081,035 B2 * | 12/2011 | Wood .............................. | 331/45 |
| 2003/0151465 A1* | 8/2003 | Wood ......................... | 331/107 SL |
| 2007/0201178 A1 | 8/2007 | Reykowski ..................... | 361/119 |
| 2008/0208031 A1* | 8/2008 | Kurpad et al. ................. | 600/410 |
| 2010/0121318 A1* | 5/2010 | Hancock et al. ............... | 606/33 |
| 2010/0148775 A1* | 6/2010 | Greim ............................ | 324/309 |
| 2010/0225404 A1* | 9/2010 | Wood .............................. | 331/57 |

* cited by examiner

*Primary Examiner* — Melissa Koval
*Assistant Examiner* — Tiffany Fetzner
(74) *Attorney, Agent, or Firm* — Schiff Hardin LLP

(57) ABSTRACT

A standing wave barrier, particularly for use in a magnetic resonance tomography device, has a body and an opening in the body that is fashioned to accommodate a cable, the opening being formed as an externally open groove along a longitudinal direction of the standing wave barrier, and is shaped so that the cable can glide in and out along the standing wave barrier through the groove.

15 Claims, 4 Drawing Sheets

STANDING WAVE BARRIER FOR A MAGNETIC RESONANCE TOMOGRAPHY DEVICE

BACKGROUND OF THE INVENTION

1. Field of the Invention

The present invention concerns a standing wave barrier to suppress standing waves on a cable, the standing wave barrier being of the type having an opening that is fashioned to accommodate the cable. Moreover, the invention concerns a magnetic resonance tomography device with a transmission antenna and a number of such standing wave barriers arranged within the transmission antenna.

2. Description of the Prior Art

Magnetic resonance tomography is a technique in widespread use for the acquisition of images of the inside of the body of a living examination subject. In order to acquire an image with this method (i.e. to generate a magnetic resonance exposure of an examination subject), the body or a body part of the patient that is to be examined must initially be exposed to an optimally homogeneous, static basic magnetic field (most often designated as a $B_0$ field) which is generated by a basic field magnet of the magnetic resonance tomography device. The basic field magnet is essentially shaped like a cylinder and is relatively long in order to achieve within it an optimally long region in which the homogeneous static basic magnetic field exists. Typically there is enough space in the cylindrical structure that a patient to be completely accommodated therein.

Rapidly switched gradient fields for spatial coding. that are generated by gradient coils, are superimposed on this basic magnetic field during the acquisition of the magnetic resonance images. Moreover, RF pulses of a defined field strength are radiated with a radio-frequency antenna into the examination volume in which the examination subject is located. This radio-frequency antenna permanently installed in the apparatus is often designated as a "transmission antenna", and additional common designations are, for example, body resonator, body coil or whole body antenna. The antenna is frequently designed in a form known as a birdcage antenna (the design of which is explained in more detail below) or as a saddle coil. The transmission antenna is localized within the basic field magnet and typically have a length between 30 cm and 60 cm.

The nuclear spins of the atoms in the examination subject are excited by the RF pulses so that they are deflected by an amount known as an "excitation flip angle" out of their equilibrium state, which runs parallel to the basic magnetic field $B_0$. The nuclear spins then precess around the direction of the basic magnetic field $B_0$. The magnetic resonance signals that are thereby generated are received by the radio-frequency reception antennas. The reception antennas can either be the same antennas with which the radio-frequency pulses were radiated, or separate reception antennas. The magnetic resonance images of the examination subject are ultimately generated on the basis of the received magnetic resonance signals. Every pixel in the magnetic resonance image is associated with a small body volume (known as a "voxel"), and every brightness or intensity value of the pixels is lined with the signal amplitude of the magnetic resonance signal that is received from this voxel.

In order to obtain an optimally good signal-to-noise ratio, the reception antennas are often formed as local coils that are separate from the transmission antennas. These local coils are optimized in terms of their geometry and their reception profile for different body regions, and are positioned optimally close to the body of the examination subject (patient). Shielded coaxial cables are typically used for the conducting the magnetic resonance signal from the local coil to a signal processing system.

In conventional magnetic resonance tomography devices, the local coil is connected with a first coaxial cable that is plugged in at a patient table. Connected with the socket of the patient table is an additional coaxial cable that conducts the magnetic resonance signal from the patient table and relays it to the signal processing system. Radio-frequency currents on the conductor shield (outside conductor) of the coaxial cable are induced due to the electrical and magnetic fields that occur during the transmission phase of the radio-frequency pulses. These currents are known as waves on a cable and, without suitable suppressing measures, can lead to image interference and—in the worst case—even to an endangerment of the patient.

For completeness, it is noted that the local coil itself can also be used as a transmission antenna in special situations. Standing waves that must then be suppressed with a standing wave barrier can arise in this case. For example, such a situation is present with head coils that are used as transmission antenna coils. However, in such a head coil the cable does not run within transmission coil (as in the permanently installed transmission coil) but rather runs past the head coil (external to the head coil), and standing waves are likewise generated in the outer conductor of the cable.

Standing wave barriers integrated into the patient bed, which represent a high-ohmic impedance Zo for the radio-frequency currents, are used to suppress the standing waves. For example, the impedance Zo can be realized by a parallel resonator. The coaxial cable is thereby wound on a coil and is connected at the ends of the winding of the conductor shield that is generated in this way with a capacitor connected in parallel with said winding. Such standing wave barriers are necessary in all conductors that lead through the transmission antenna. Such a known standing wave barrier 1 is depicted in FIG. 5. A coaxial cable 2 with a conductor shield 4 that is open to the outside and that surrounds a plurality of inner conductors 3 is would on a coil 26. The coil 26 is connected at both of its ends with terminals of a first capacitor 14 with whose help the resonance of the parallel oscillating circuit that is formed in this way can be adjusted. The inner conductors 3 are insulated in a conventional manner from the conductor shield 4.

The impedance Zo can also be realized by a $\lambda/4$ wave trap (see FIG. 6). In such a solution, a copper tube 27 with a length L is slid over the outer conductor 4 of the cable 2. One end—at the one opening—of the copper tube 27 is directly soldered with the outer conductor (see first solder point 28) and the other end—at the other opening—of the copper tube 27 is electrically connected with the outer conductor 4 via what are known as shortening capacitors (see first capacitor 14) that on the one end are soldered with the external conductor 4 and on the other end are soldered with the copper tube 27 (see second solder point 29). In many cases, multiple signal-conducting inner conductors 3 are also merged and surrounded with a single outer conductor 4. The expression "shortening capacitor" actually originates from radio engineering and there designates a capacitor that serves to electrically shorten antennas. There it is connected in series with the antenna and should be of optimally high quality.

The radio-frequency current (RF current) I that forms the standing wave to be suppressed and flows in the outer conductor 4 is also visualized in FIGS. 5 and 6. Both embodiments of the standing wave barrier according to the prior art that are described in the preceding are characterized by, during operation of the magnetic resonance tomography device, the standing wave barriers mounted at or in the patient bed being moved through the transmission antenna together with the patient and the local coils.

In the known solution to suppress the standing waves, a significant number of standing wave barriers at relatively short intervals relative to one another is consequently necessary in order to ensure the desired suppression of the standing waves along the entire length of the patient bed that is usable within the transmission antenna. This solution can be relatively complicated, and therefore also expensive. Furthermore, an optimally flexible use of the patient bed is not ensured because the integrated standing wave barriers can only be tuned to a resonance frequency. Therefore, a patient bed that is adapted to a resonance tomography device operated with 1.5 Tesla (magnetic resonance frequency for $H^+$ nuclei=62.66 MHz) cannot be used in a magnetic resonance tomography device operating with 3 Tesla, for example (magnetic resonance frequency for $H^+$ nuclei=125.32 MHz), but such alternative use would be desirable. An additional disadvantage is the fact that the outer conductor 4 is a fixed and precisely localized component of the standing wave barrier.

It is noted that different realizations for standing wave barriers are known in other technical fields of engineering. For example, isolating transformers, capacitive couplers as well as ferrite core chokes are known, by every solution entails inherent advantages and disadvantages. For example, ferrite core-based solutions in which a cable is directed through an opening in the ferrite core so that the ferrite core completely surrounds the cable, cannot be used in magnetic resonance tomography because the ferrite cores would be driven to saturation due to the relatively high magnetic field.

SUMMARY OF THE INVENTION

It is an object of the present invention to further develop a standing wave barrier of the aforementioned type as well as a magnetic resonance tomography device with a number of such standing wave barriers, such that the problems cited above are remedied.

According to the invention, a standing wave barrier has a body and an opening in the body that is fashioned to accommodate the cable, the opening forming an externally open groove along a longitudinal direction (extent) of the standing wave barrier, and the opening is shaped to allow the cable to glide in and out along the standing wave barrier through the groove.

According to the invention, the standing wave barrier is used in a magnetic resonance tomography device and forms a component of a magnetic resonance tomography device according to the invention that has a transmission antenna and a number of the standing wave barriers according to the invention.

The number of standing wave barriers can be a single standing wave barrier or multiple standing wave barriers. With regard to the number it is merely required that the effect of the standing wave barrier is asserted along the effective (in many cases the geometric) length of the transmission antenna. Depending on the length of a standing wave barrier, the number of standing wave barriers to be selected thus results depending on a given length of, for example, the permanently installed transmission antenna. Every standing wave barrier independently causes a fluctuation of a current distribution in the conductor shield of the cable, with the goal of reducing or, respectively, limiting the amplitude of the RF current to a certain degree. For example, given a single, relatively long standing wave barrier, a relatively high maximum and a minimum will occur in the current distribution. Given use of two or more standing wave barriers, a corresponding number of minima and maxima will be obtained so that the maximum amplitude is correspondingly reduced given an increasing number.

However, since a flexibly positionable (thus not permanently mounted) local coil can also act as a transmission coil, the standing wave barrier according to the invention can also be used to suppress the standing wave caused by the local coil. Since local coils are normally relatively short in relation to a stationary transmission coil, often a single standing wave barrier or possibly two such standing wave barriers is already sufficient in order to achieve the necessary suppression.

With regard to the suppression of standing waves, the standing wave barrier according to the invention acts like a $\lambda/4$ wave trap, but with the design difference that no galvanic connection between the outer conductor and the standing wave barrier is necessary and the cable is not completely enclosed. In operation, the standing wave barrier inductively couples with the outer conductor of the cable and allows a good shielding of the standing wave barrier similar to that with the $\lambda/4$ wave trap, such that in practice no negative effect on measurement results or the performance of the magnetic resonance tomography device is to be expected. The standing wave barrier according to the invention primarily allows a complete mechanical decoupling of the standing wave barrier from the cable to be effected by the standing wave barrier. The barrier effect of the standing wave barrier is additionally no longer dependent on the shield of the cable. Therefore, the cable can now be moved uncoupled from the standing wave barrier and, for example, slide out of or into the groove. Therefore cables entirely covered with plastic can also be used. However, surfaces facing the cable and covered with plastic can also be provided if cables with an uncovered metal braiding outer conductor are used. Given a corresponding dimensioning of the groove, a plurality of cables can also be accommodated in it. Since the cable is no longer a component of the standing wave barrier, it can now be tested uncoupled from said standing wave barrier and be tuned to the respective magnetic resonance frequency. At the same time, the patient bed can be moved independent of the standing wave barrier.

Due to the more flexible utility of the patient bed and the constructive design of the standing wave barrier, and the decoupling of the standing wave barrier from the patient bed, a significant cost savings results from an economic standpoint, and not only in the manufacturing of both the standing wave barrier and the magnetic resonance tomography device but also in the operation of the magnetic resonance tomography device.

With regard to the cross section or, respectively, the cross section shape of the groove, a significantly polygonal U-shape or a U-shape executed with rounded edges can be provided. A V-shaped embodiment of the cross section of the groove is likewise possible. However, it has proven to be particularly advantageous when the cross section of the groove possesses a circle segment shape, for example that of a semicircle. A higher quality of the wave trap is thereby attained because relatively low magnetic losses in the magnetic circuit occur given this shape. However, oval or other shapes are also applicable.

In a functional analogy to the prior art, according to which the outer conductor of the cable realizes a reflux of the current given known standing wave barriers, in the standing wave barrier according to the invention it is provided in an advantageous manner that the groove possesses a first metalized layer on or below its surface facing toward the accommodated cable, which metalized layer takes over the current circulation at the point of the outer conductor of the cable.

According to a further aspect of the invention, the body of the standing wave barrier possesses a second metalized layer at or below its surfaces situated outside of the groove. This second metalized layer enables a current flow while still providing a shielding effect which permits practically no scatter field to escape from the standing wave barrier via these surfaces, and thus interferences with the magnetic resonance tomography device due to such scatter fields are avoided in practice.

In order to avoid leakage of the magnetic field that exists in the body of the standing wave barrier during operation while enclosing of the conductor accommodated in the standing wave barrier, the standing wave barrier has a first gap running along the groove, adjacent to said groove and on one side of the groove, and a second gap running along the groove, likewise adjacent to the groove and on the other side of said groove. The two gaps interrupt the metalized second layer at their positions on the surface of the body of the standing wave barrier. Depending on the orientation, the magnetic field can escape or enter through these gaps and thus forms a closed field line around the cable.

In order to tune the resonance frequency of the standing wave barrier to adapt it to a desired value, the standing wave barrier according to the invention is fashioned such that the second metalized layer is interrupted by at least one third gap that runs transversely to the longitudinal direction of the standing wave barrier in the circumferential direction of the body with the exception of the groove. The third gap produced in this way is bridged by at least one first capacitor. The metalized layers adjoining the third gap are thus contacted with a respective terminal of the capacitor. According to this design, inductive elements that—together with the capacitor—form a parallel resonator that is matched to the desired resonance frequency are achieved with the aid of the metalized surface of the body. It is noted that a realization without capacitors is also conceivable if the capacitance attained by the third gap is sufficient to achieve the desired magnetic resonance frequency.

In a further exemplary embodiment of the invention, the standing wave barrier is fashioned with the metalized first layer interrupted by a first gap running along the groove on one side of the groove and interrupted on the other side of the groove by a second gap running along said groove. The two gaps which enable an escape or entrance of the magnetic field surrounding an accommodated cable, and are not arranged on the outer facing surfaces of the body of the standing wave barrier but rather are embodied within the groove, for example in its outer edge region. This aspect of the invention has a positive effect on the shielding behavior of the magnetic field that compensates (cancels) the standing wave, since the air gap that is to be bridged is shorter than in the case of an arrangement of the two gaps at positions of the surface of the body that are situated outside of the groove. In order to intensify the shielding effect, the depth of the groove can be increased. If necessary, the side walls of the body can be enlarged to accommodate such an increased depth.

For example, the standing wave barrier can be realized by metalized or metallic layers forming the body, such that the body itself has a void that is spatially bounded by the metalized layers. However, it has proven to be advantageous for the body to be produced at least in part from a plastic that has appropriate properties in order to make it usable in radio-frequency applications. Such a plastic body then acts as a mechanical support for the metalized layers or surfaces provided on or in it, and increases the mechanical rigidity of the standing wave barrier, and consequently also its mechanical durability. In one embodiment of such a body based on plastic, metalized layers can be located on its surface or below its surface (for example sealed). If the external surfaces below which the metalized layers are located are formed by plastic, the insulating effect and the protective effect of the plastic also advantageously come into play in addition to the mechanically stabilizing effect.

The standing wave barriers according to the invention can be entirely or partially attached to or in a patient bed in a magnetic resonance tomography device. According to a preferred exemplary embodiment of the invention, however, the number of standing wave barriers within the permanently installed transmission coil is likewise permanently installed, and the standing wave barriers are preferably connected with a support of the transmission antenna so as to be stationary. The number of standing wave barriers can be selected or limited such that the total length of the number of standing wave barriers corresponds precisely to the geometric or effective length of the transmission antenna, which will in the normal case be significantly shorter than the length of the patient bed. A significant cost savings is thereby achieved. At the same time the patient bed is enabled for use with different magnetic resonance tomography devices because it no longer has frequency-dependent components matched to a specific device. The behavior of the complete system is also benefited because the influence on the transmission antenna is now independent of the position of the patient bed, which no longer has any frequency-dependent modules.

As noted above, in the use of the standing wave barrier according to the invention in a magnetic resonance tomography device, the sum length of the number of standing wave barriers is at least as long as the geometric length of the transmission antenna. It has proven to be particularly advantageous, however, for the sum length of the standing wave barriers to be at least as long as the effective length of the transmission antenna, which in the normal case is greater than the geometric length of the transmission antenna. It is thereby ensured that the required suppression of the standing waves by the standing wave barriers, or a chain of such standing wave barriers, is ensured in regions of a cable in which standing waves can arise due to the field of the transmission antenna.

According to a special embodiment of the invention, a chain of standing wave barriers is installed in a magnetic resonance tomography device according to the invention. This can ensue such that individual standing wave barriers are positioned with an interval relative to one another. The standing wave barriers preferably are directly strung one after another without intervals, so that their facing surfaces (facing toward one another) contact in an electrically conductive manner. Adjacent, localized second metalized layers can thus exist, but preferably one of these can be omitted so that a single second metalized layer forms a common facing surface or precise inner separation surfaces of two adjacent standing wave barriers. A first metalized layer running along the number of standing wave barriers thereby arises within the continuous groove, this first metalized layer connecting the individual standing wave barriers with one another in an electrically conductive manner. This first metalized layer lining or forming the common groove can alternatively be produced separately and be contacted with the second metalized layers in order to achieve a structure with identical effect. With this embodiment it is ensured that the blocking effect is not altered in practice even given a cable sliding out of or into the groove at segments, and at the same time the mechanical stability of the chain of the standing wave barriers is beneficially affected.

DESCRIPTION OF THE PREFERRED EMBODIMENTS

Figure 1:
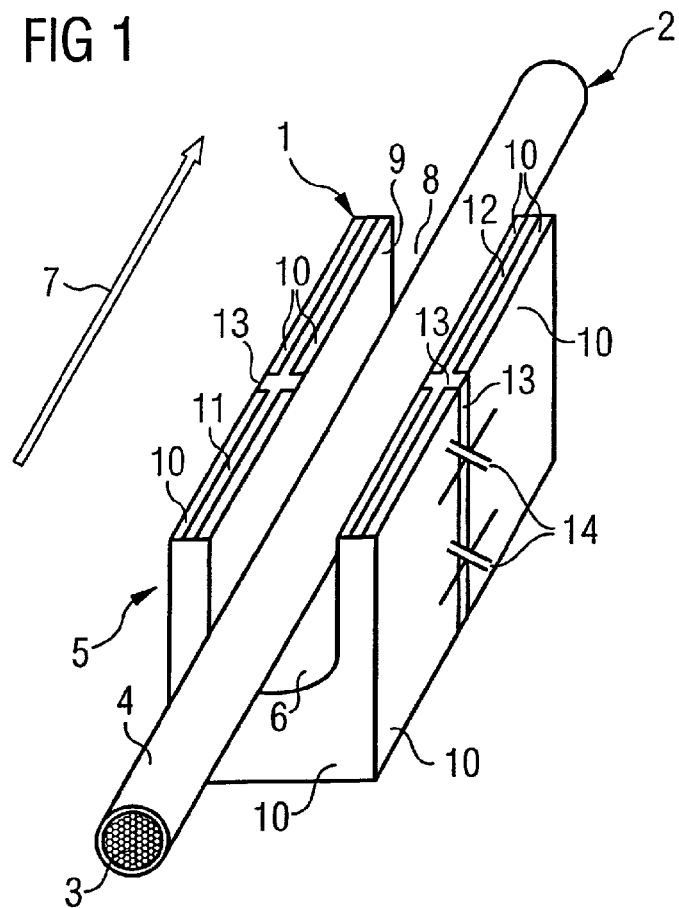
FIG. 1 shows a standing wave barrier according to a first exemplary embodiment of the invention.

A standing wave barrier 1 according to the invention, in which a cable 2 is placed, is shown in FIG. 1.

The cable 2 has an inner conductor that, in operation, typically directs signals and an outer conductor 4 that has a shielding effect on the inner conductor 3. The shielding effect is realized by a wire mesh that surrounds the inner conductor 3. The inner conductor 3 is insulated from the outer conductor 4.

The standing wave barrier 1 has a body 5 that, in the present case, is realized by an RF-capable plastic. The body 5 has an opening 6 that is fashioned to accommodate the cable 2. The opening 6 has a groove 8 running along a longitudinal direction 7 of the standing wave barrier 1 and open to the outside. The groove 8 is produced such that the cable 2 can slide out or in along the standing wave barrier 1 through the groove 8. The groove 8 has a first metalized layer 9 on its surface facing toward the accommodated cable 2.

The other surfaces or sides of the body 5 that are situated outside of the groove 8 have a second metalized layer 10. The second metalized layer 10 runs on the upper facing surface of the body 5 adjacent to the groove 8, on the left (not visible) and right lateral surfaces of the body 5 that adjoin the upper facing surface, on the front and rear (not visible) facing surfaces of the body 5, and on the lower (not visible) side of the body 5. A first gap 11 and a second gap 12 are provided on the facing surface of the body 5 projecting upward relative to the plane of the drawing, so the two gaps 11 and 12 interrupt the second metalized layer 10. The two gaps 11 and 12 run parallel to the apparatus 8 along the left and right side of the groove 8. The second metalized layer 10 is additionally interrupted by a third gap 13 that runs transversal to the longitudinal direction 7 of the standing wave barrier 1 in the circumferential direction of the body 5, with the exception of the groove 8. The third gap 13 accordingly extends across the two gaps 11 and 12 on the upper facing surface of the body 5, on the left and right lateral surfaces of the body 5 that adjoin the upper facing surface, and on the underside of the body 5.

This third gap 13 is bridged by at least one capacitor (precisely two first capacitors 14 in the present case, however). At which point the first capacitor 14 bridges the third gap 13 is thereby basically a question of the basic design conditions. In principle, a single first capacitor 14 can be provided. However, with regard to the suppression effect on the standing waves it can be advantageous when more than one first capacitor 14 is provided. The plurality of these first capacitors 14 can advantageously be distributed uniformly along the third gap 13.

The standing wave barrier 1 according to the invention functions as a $\lambda/4$ wave trap, but without galvanic connection with the outer conductor 4 of the cable 2 and without completely enclosing the cable 2.

Figure 3:
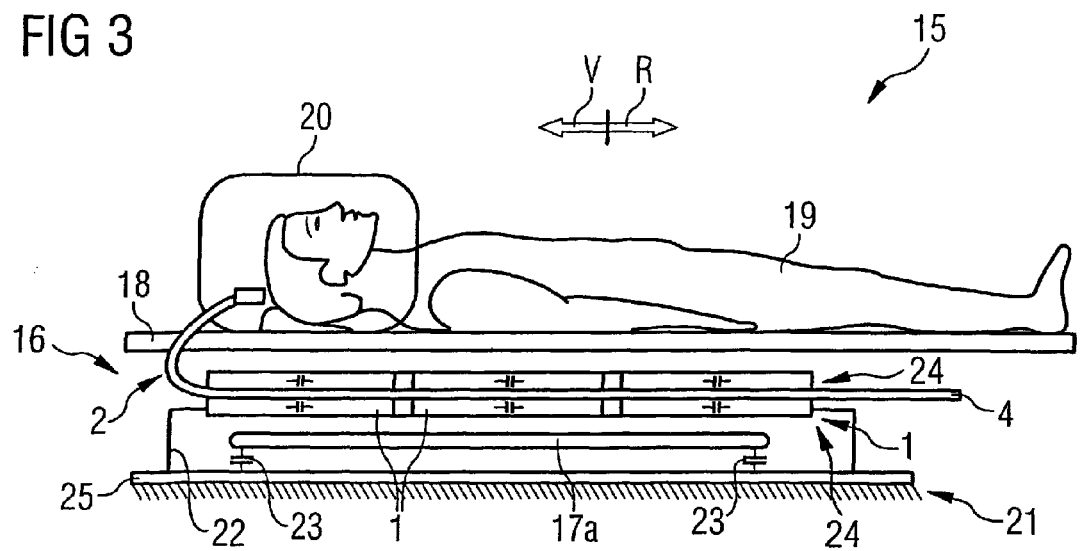
FIG. 3 shows, analogous to FIG. 2, a patient bed of a magnetic resonance tomography device with a number of standing wave barriers according to FIG. 1.
Figure 4:
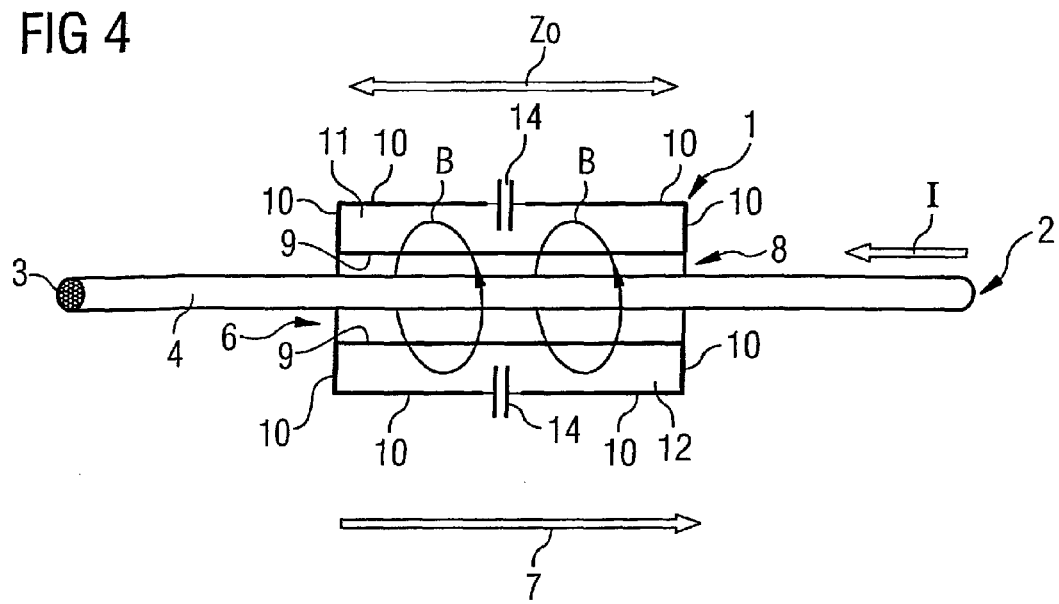
FIG. 4 schematically illustrates, in a simplified manner, the effective principle of the standing wave barrier according to FIG. 1.
Figure 5:
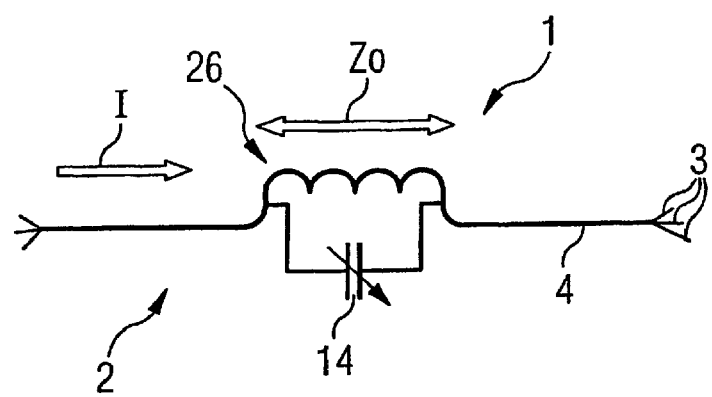
FIG. 5 schematically illustrates a first embodiment of a standing wave barrier according to the prior art.
Figure 6:
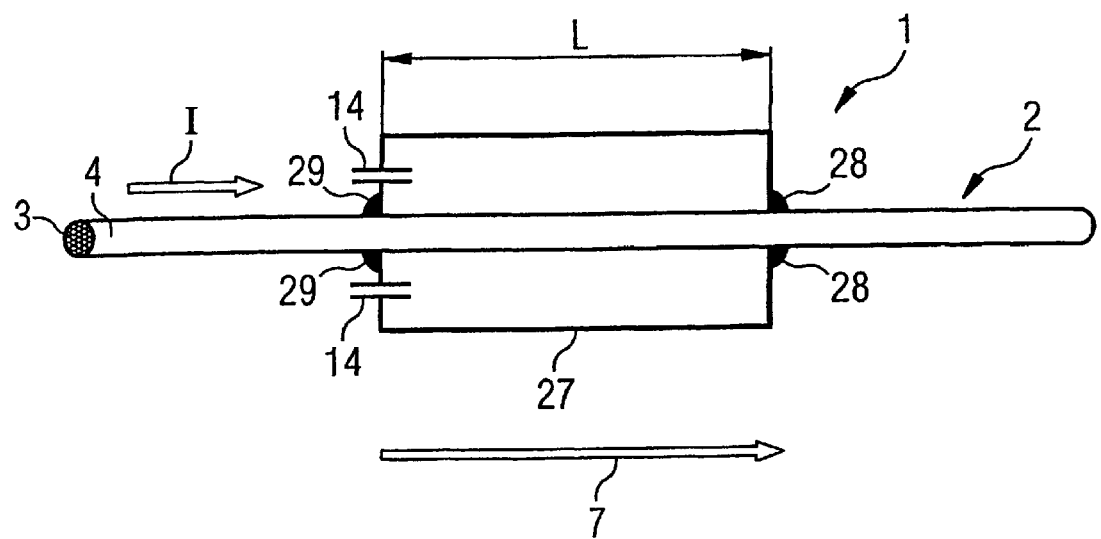
FIG. 6 schematically illustrates a second embodiment of a standing wave barrier according to the prior art.

The mode of operation of the standing wave barrier 1 is presented in principle in FIG. 4 in a significantly simplified manner. As is apparent in FIG. 3, the metalized layers 9 and 10 in the drawing plane of FIG. 4 form continuous electrical conductors whose ends are connected at the outlying surfaces of the body 5 with the use of the first capacitors 14 across the third gap 13. The same applies for the underside of the body 5 which is localized in the drawing plane below the cable 2. A parallel resonator is thus realized that possesses an inductive component and a capacitive component, wherein the desired resonance frequency is set with the aid of the first capacitors 14. The metalized layers 9 and 10 which realize the continuous copper conductor now allow a current circulation in the parallel resonator that, for its part, drives a magnetic field B that completely surrounds the cable 2 and on the other hand acts on the outer conductor 4 such that the standing waves are suppressed. As is schematically shown in FIG. 4, the magnetic field B exits the body 5 from the second gap 12 and enters the body 5 through the first gap 11. The air gap formed between the gaps 11 and 12 is essentially the single region in which the magnetic field B leaves the body 5, since the metalized layers 9 and 10 prevent escape of the magnetic field B from the body 5 at other points of the body 5. In contrast to a conventional $\lambda/4$ wave trap, however, in the present case the first metalized layer 9 within the groove 8 is responsible for the current transport that would ensue via the outer conductor 4 of the cable 2 given a conventional $\lambda/4$ wave trap (see FIG. 6). Blocking effects that are just as significant (thus in the range >25 database), can be achieved with the standing wave barrier 1 according to the invention, as with conventional standing wave barriers.

With regard to the dimensions of the body 5, it is mentioned for example that a height of 5 cm, a width of 3 cm and a length of 20 cm are appropriate examples for a diameter of the cable 2 of approximately 0.8 cm. The inner width of the groove 8 can be 1 cm and the depth of the groove 8 can be 4 cm. These values describe only the dimensions of the standing wave barrier 1 according to the first exemplary embodiment, and are not limiting nor to be construed as limiting.

Figure 2:
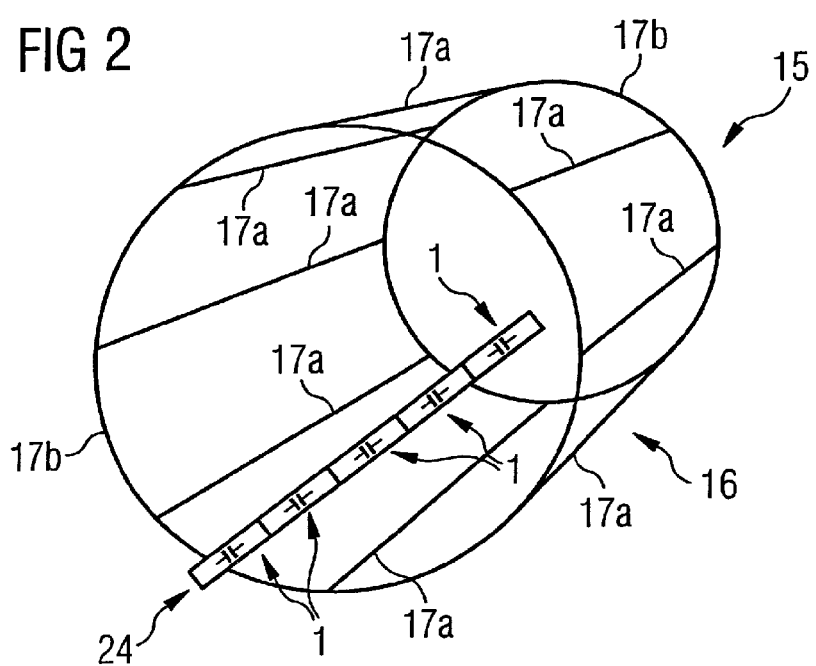
FIG. 2 shows a transmission antenna of a magnetic resonance tomography device in a severely schematized manner, with a number of standing wave barriers according to FIG. 1.

Shown in FIG. 2 in simplified form is a transmission antenna 16 according to one possible embodiment, namely as a birdcage transmission antenna of a magnetic resonance tomography device 15. The transmission antenna 16 has eight conductive rods 17a that are attached to two rings 17b that form a return conductor for the current in the rods 17a. Such a birdcage antenna can but does not need to be, surrounded by an additional copper shield and operates without additional capacitors.

Located on the inside of the transmission antenna 16 are five standing wave barriers 1 that form a standing wave barrier chain 24. In order to suppress the effect of the transmission antenna 16 of such a magnetic resonance tomography device 15 that is caused by the standing waves, it is advantageous for the total length of the number of standing wave barriers 1 to be at least as long as the effective length of the transmission antenna 16. Typically, this length is greater than the geometric or physical length of the transmission antenna 16. In the present case, this is formed by five standing wave barriers 1 that—with regard to their sum length—project beyond the length of the transmission antenna 16. If the transmission antenna 16 is thus approximately 30 cm long, the sum length of the number of standing wave barriers 1 can amount to approximately 40 cm, for example, in order to effectively suppress the standing waves.

In contrast to the prior art, the chain 24 of standing wave barriers 1 according to the invention is stationary and positioned at a fixed location within the fixed transmission antenna 16.

This is indicated but not explicitly depicted in FIG. 2 and is explicitly depicted in FIG. 3. Three standing wave barriers 1 are shown in FIG. 3. According to FIG. 3, the standing wave barrier chain 24 is fixed, detached from a recumbent board 18, and connected in a stationary manner with a support device 21 of the transmission antenna 16 of the magnetic resonance tomography device 15 via an attachment device 22.

Furthermore, a patient 19 positioned on the recumbent board 18 is shown in FIG. 3. The head of the patient 19 is covered with a local coil 20 with whose help nuclear spin signals which are excited in the head of the patient 19 with the aid of the stationary transmission antenna 16 are received and are relayed via the cable 2 connected to the local coil 20 to a signal processing system (not shown for reasons of clarity). The three standing wave barriers 1 arranged in series form the standing wave barrier chain 24. The advantageous embodiment of the individual standing wave barriers 1 now enables a forward and backward movement of the patient bed 18, which is indicated by the arrows V (forwards) and R (backwards). Given these movements, the cable 2 is raised out of the groove 8 or, respectively, inserted into the groove 8 dependent on the position variation of the recumbent board 18. A complete mechanical and galvanic decoupling between the standing wave barrier 1 and the outer conductor 4 of the cable 2 is achieved via the free mobility of the cable 2. It is only the inductive coupling between the standing wave barrier 1 and the outer conductor 4 of the cable 2 that produces the desired suppression of the standing waves.

For completeness in the explanation of FIG. 3, it is noted that in FIG. 3 the conductor rod 17a of the transmission antenna 16 is shown, but in the present case a different type of transmission antenna 16 is shown from that in FIG. 2, but this is not pertinent to the objects of the invention. In the present case, the ends of the conductor rod 17a are connected with ground area 25 by two capacitors 23 so that a frequency adaptation with regard to the transmission antenna 16 is achieved.

Figure 7:
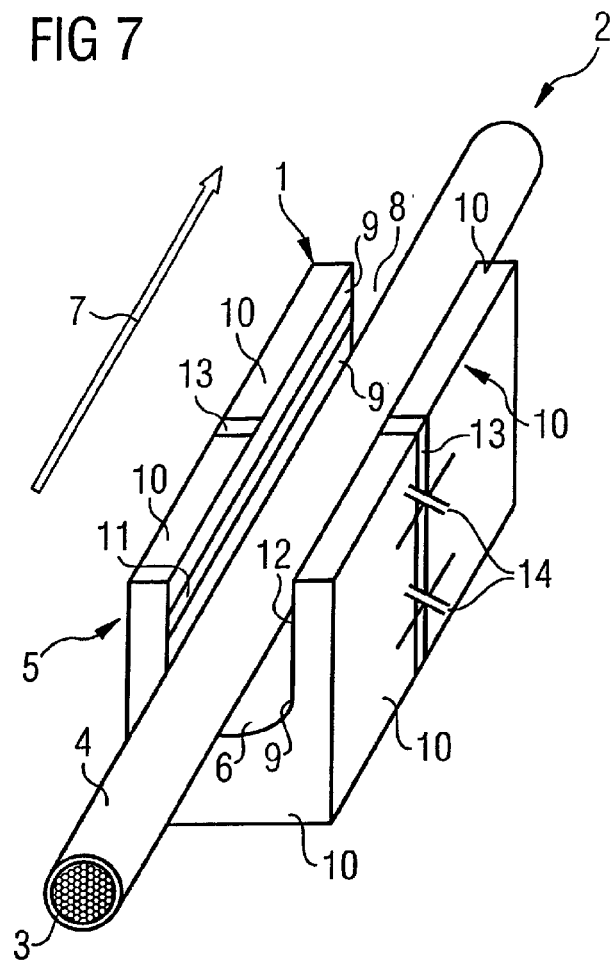
FIG. 7 shows a standing wave barrier according to a second exemplary embodiment of the invention.

In an additional exemplary embodiment of the invention that is shown in FIG. 7, the first gap 11 and the second gap 12 are not localized at the outer faces or surfaces of the body that now are continuously covered with the second metalized layer 10, but rather are localized within the groove 8. These gaps 11 and 12 determine the position of the exit and the entrance of the magnetic field B and can also be localized in transition regions between the outer facing surface 5 of the body 5 and the groove 8. Their position affects the field distribution of the magnetic field B existing outside of the body. The width of the gaps 11 and 12 measured transverse to the longitudinal direction 7 can be used to affect the field distribution so that scatter fields are avoided or reduced.

In a further exemplary embodiment of the invention, it can be provided that a number of standing wave barriers 1 have a groove 8 connecting the standing wave barriers 1. This connecting groove 8 can be produced by the now continuous first metalized layer 9 (thus a first metalized layer spanning individual standing wave barriers 1) that forms a conductive rail or surface made of metal, which produces a compact execution and a greater stability of the standing wave barrier chain 24. A standing wave barrier chain 24 achieved in such a manner can also be sealed in a block of RF-compatible plastic.

Figure 8:
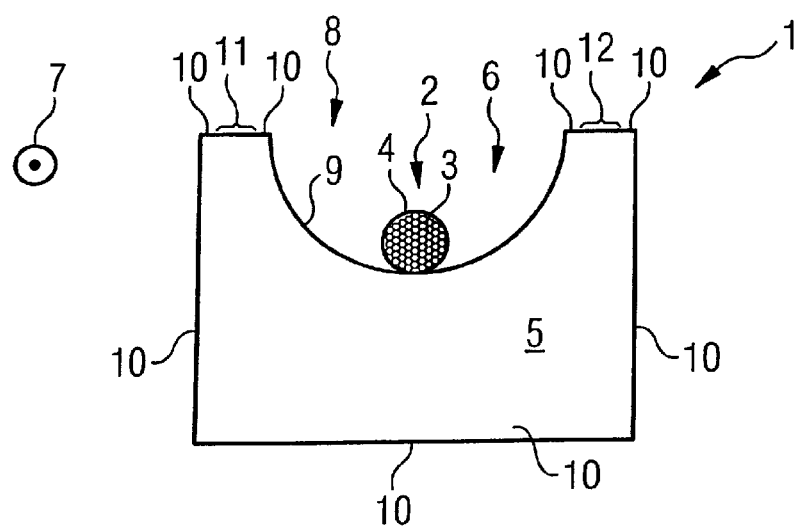
FIG. 8 shows a standing wave barrier according to a preferred exemplary embodiment of the invention with a groove shaped as a circle segment.

According to a preferred exemplary embodiment of the invention, the profile of the groove 8 running transverse to the longitudinal direction 8 is formed in the shape of a circle segment so that magnetic losses are kept as low as possible. The standing wave barrier 1 according to this exemplary embodiment is shown on the front face of the body 5 in a frontal view in FIG. 8. According to this exemplary embodiment, the insertion and extraction of the cable 2 is also significantly simplified.

With regard to the width of the third gap 13 as measured in the longitudinal direction 7, it is noted that this width must be selected so that the required electrical breakdown resistance is ensured.

The metalized layers 9 and 10 are preferably made of copper, but any other metal, any metal alloy or—very generally—any conductive material can be used, as long as the inductive effect of these layers 9 and 10 that is required for the parallel resonator is achieved.

With regard to the shape of the body 5, it is noted that the body 5 in the exemplary embodiments herein has been depicted as having sharp edges; but body shapes with rounded edges are also suitable. Likewise, the external shape of the body 5 with regard to its longitudinal direction 7 can deviate from a flat surface, which analogously also applies for the shape of the groove 8. The groove 8 can furthermore be covered by a plastic layer so that abrasion of the cable 2 or cables 2, and the danger of damage to the first metalized layer 9 or to the cable 2 that would result from such an abrasion, are reduced or entirely avoided.

With regard to the attachment of the standing wave barriers 1, it is noted that this can ensue at objects of the magnetic resonance tomography device different than those disclosed herein that are themselves fixed in location, such that the standing wave barriers 1 are also fixed in location relative to the transmission antenna 16.

The embodiment of standing wave barrier 1 described in detail in the preceding are only specific exemplary embodiments and can be modified in the most varied manners by those skilled in the art without departing from the scope of the invention. Although the standing wave barrier 1 according to the invention has been explained herein in connection with a magnetic resonance tomography device 15, other devices or uses of the standing wave barrier 1 according to the invention will be apparent to those skilled in the art based on the present description. In particular, in addition to applications in medical technology, applications are possible in any non-medical technical field of engineering in which standing wave barriers 1 play a role and a cable 2 must be moved into or out of a standing wave barrier 1. The invention can therefore also be used in scientific and/or industrial applications.

I claim as my invention:

1. An standing wave barrier configured to suppress standing waves on an electrically conducting cable, said standing wave barrier comprising:

a body configured to interact with an electrically conducting cable in order trap standing waves onset electrically conducting cable, said body having an opening therein; and said opening in said body being shaped as an externally open groove in said body extending along a longitudinal direction of said body and having a shape that allows an electrically conductive cable in said groove to glide in and out of said body through said groove in said longitudinal direction, with no galvanic connection and no fixed mechanical coupling between said electrically conducting cable and said body.

2. A standing wave barrier as claimed in claim 1 wherein said groove has a shape conforming to a segment of a circle.

3. A standing wave barrier as claimed in claim 1 wherein said groove has a groove surface facing toward said cable, and wherein said body comprises a metalized layer on or below said groove surface.

4. A standing wave barrier as claimed in claim 3 wherein said metalized layer is a first metalized layer, and wherein said body comprises body surfaces situated outside of said groove, and comprises a second metalized layer at or below said body surfaces situated outside of said groove.

5. A standing wave barrier as claimed in claim 4 wherein said second metalized layer is interrupted by a first gap in said body proceeding along and adjacent to said groove on a first side of said groove, and by a second gap in said body proceeding along and adjacent to said groove at a second, opposite side of said groove.

6. A standing wave barrier as claimed in claim 5 wherein said second metalized layer is interrupted by a third gap proceeding transverse to said longitudinal direction of said body and proceeding in a circumferential direction of said body except for said groove, and a capacitor bridging said third gap.

7. A standing wave barrier as claimed in claim 4 wherein said second metalized layer is interrupted by a gap proceeding transverse to said longitudinal direction of said body and proceeding in a circumferential direction of said body except for said groove, and a capacitor bridging said gap.

8. A standing wave barrier as claimed in claim 3 wherein said metalized layer is interrupted by a gap proceeding along and within said groove at a first side of said groove, and is interrupted by a second gap proceeding along and within a second, opposite side of said groove.

9. A standing wave barrier as claimed in claim 1 wherein said body is at least partially comprised of plastic.

10. A magnetic resonance tomography apparatus comprising:
a magnetic resonance data acquisition device comprising
at least one electrically conducting cable in which a standing wave is produced during operation of said magnetic resonance data acquisition device; and
a standing wave barrier comprising a body configured to interact with an electrically conducting cable in order to trap standing waves onset electrically conducting cable, said body having an opening therein shaped in order to accommodate said electrically conducting cable therein, said opening being formed as an externally open groove extending a longitudinal direction of said body and having a shape that allows said electrically conducting cable to glide in and out along said standing wave barrier through said groove in said longitudinal direction, with no galvanic connection and no fixed mechanical coupling between said electrically conducting cable and said body.

11. A magnetic resonance tomography apparatus as claimed in claim 10 wherein said magnetic resonance data acquisition unit comprises
a transmission antenna embodying said cable, and
wherein said standing wave barrier is a first standing wave barrier, and comprising
a plurality of additional standing wave barriers, identical to said first standing wave barrier, located relative to said transmission antenna in order to suppress standing waves arising during operation of said transmission antenna.

12. A magnetic resonance tomography apparatus as claimed in claim 11 wherein said transmission antenna is permanently installed in said magnetic resonance data acquisition unit, and wherein said first standing wave barrier and said plurality of additional standing wave barriers are permanently installed within said transmission antenna.

13. A magnetic resonance tomography apparatus as claimed in claim 11 wherein said transmission antenna is supported in said magnetic resonance data acquisition unit by a support device, and wherein said first standing wave barrier and said plurality of additional standing wave barriers are connected in a stationary manner with said support device.

14. A magnetic resonance tomography apparatus as claimed in claim 10 wherein said transmission antenna has an effective length, and wherein said first standing wave barrier and said plurality of additional standing wave barriers, in combination, have a sum length that is at least as long as said effective length of said transmission antenna.

15. A magnetic resonance tomography apparatus as claimed in claim 11 wherein said first standing wave barrier and said plurality of additional standing wave barriers are electrically connected with each other by a metalized layer continuously proceeding along the respective grooves of said first standing wave barrier and said plurality of additional standing wave barriers.

\* \* \* \* \*